(12) United States Patent
Berme et al.

(10) Patent No.: US 9,854,997 B1
(45) Date of Patent: Jan. 2, 2018

(54) FORCE MEASUREMENT SYSTEM

(71) Applicant: Bertec Corporation, Columbus, OH (US)

(72) Inventors: Necip Berme, Worthington, OH (US); Benjamin Robert Hoffman, Columbus, OH (US); Sasan Ghassab, Columbus, OH (US)

(73) Assignee: Bertec Corporation, Columbus, OH (US)

(*) Notice: Subject to any disclaimer, the term of this patent is extended or adjusted under 35 U.S.C. 154(b) by 0 days.

(21) Appl. No.: 15/283,382

(22) Filed: Oct. 1, 2016

Related U.S. Application Data

(60) Provisional application No. 62/252,469, filed on Nov. 7, 2015.

(51) Int. Cl.
*A61B 5/11* (2006.01)
*A63B 22/02* (2006.01)
(Continued)

(52) U.S. Cl.
CPC ............ *A61B 5/112* (2013.01); *A61B 5/1036* (2013.01); *A63B 22/0285* (2013.01);
(Continued)

(58) Field of Classification Search
CPC ........ G01G 19/52; G01G 19/62; G01G 11/00; G01G 11/02; G01G 11/025; G01G 11/04;
(Continued)

(56) References Cited

U.S. PATENT DOCUMENTS

| 406,314 | A | * | 7/1889 | Souder | ................... B66B 21/08 198/327 |
| 2,823,785 | A | * | 2/1958 | Hefti | ...................... B66B 21/06 198/328 |

(Continued)

FOREIGN PATENT DOCUMENTS

DE 4027317 C1 * 12/1991 ........... A61B 5/1038

OTHER PUBLICATIONS

NKK website, "Horizontal Circular-type Metal-Pallet Moving Walkway Developed", dated Sep. 28, 1999, retrieved from <http://www.jfe-holdings.co.jp/en/release/nkk/39-7/art04.html> on Jul. 30, 2017.

(Continued)

*Primary Examiner* — David J McCrosky
(74) *Attorney, Agent, or Firm* — The Law Office of Patrick F. O'Reilly, III, LLC

(57) ABSTRACT

A force measurement system includes a plurality of force measurement assemblies arranged in a loop configuration, the plurality of force measurement assemblies configured to be displaced around a continuous path of movement such that a particular one of the plurality of force measurement assemblies that is disposed underneath a subject varies over time. Each of the plurality of force measurement assemblies includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject. The force measurement system may additionally comprise a data processing device operatively coupled to each of the force transducers of each of the force measurement assemblies.

8 Claims, 13 Drawing Sheets

(51) Int. Cl.
*A61B 5/103* (2006.01)
*A61B 5/00* (2006.01)
*G01G 19/52* (2006.01)
*B65G 17/06* (2006.01)

(52) U.S. Cl.
CPC ........... *A61B 5/1038* (2013.01); *A61B 5/6887* (2013.01); *A63B 2220/51* (2013.01); *A63B 2220/52* (2013.01); *B65G 17/068* (2013.01); *G01G 19/52* (2013.01)

(58) Field of Classification Search
CPC .... G01G 11/043; G01G 11/046; G01G 11/06; G01G 11/065; A61B 5/1036; A61B 5/1038; A63B 2220/51; A63B 2220/52; A63B 2220/53; A63B 22/02; A63B 22/0235; A63B 22/0285; A63B 24/0062; A63B 24/0065; A63B 24/0068; A63B 24/0071; B66B 21/00; B66B 21/04; B66B 21/06; B66B 21/08; B66B 21/10; B66B 23/08; B66B 23/10; B66B 23/12; B66B 23/147; B66B 2023/142; B65G 17/066; B65G 17/068; B65G 17/086; B65G 17/385
USPC ................... 73/172; 600/587, 595; 177/145; 197/324, 328, 332, 333
See application file for complete search history.

(56) References Cited

U.S. PATENT DOCUMENTS

| | | | |
|---|---|---|---|
| 3,395,648 A | 8/1968 | Karr el al. | |
| 3,410,390 A | 11/1968 | Petersen | |
| 3,515,253 A * | 6/1970 | Saburo | B65G 17/066 198/328 |
| 3,939,959 A * | 2/1976 | Dunstan | B66B 21/12 198/334 |
| 6,038,488 A | 3/2000 | Barnes et al. | |
| 6,113,237 A | 9/2000 | Ober et al. | |
| 6,123,647 A * | 9/2000 | Mitchell | A63B 22/02 482/54 |
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,899,216 B2 * | 5/2005 | Levy | B66B 21/06 198/328 |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2014/0190789 A1 | 7/2014 | Clarke | |
| 2015/0096387 A1 | 4/2015 | Berme et al. | |
| 2015/0274490 A1 | 10/2015 | Vlad | |
| 2016/0245711 A1 | 8/2016 | Berme et al. | |

OTHER PUBLICATIONS

First office action on the merits (Non-Final Rejection) in U.S. Appl. No. 15/641,659, dated Aug. 1, 2017.

* cited by examiner

FORCE MEASUREMENT SYSTEM

CROSS-REFERENCE TO RELATED APPLICATIONS

This patent application claims priority to, and incorporates by reference in its entirety, U.S. Provisional Patent Application No. 62/252,469, entitled "Force Measurement System", filed on Nov. 7, 2015.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force measurement systems. More particularly, the invention relates to a force measurement system that comprises a plurality of force measurement assemblies configured to be displaced around a continuous path of movement.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

Conventional force measurement systems have numerous limitations and drawbacks. For example, conventional force measurement systems comprising typical force plates are stationary, and thus do not easily accommodate a subject walking or running thereon. To overcome this limitation, a large array of adjacent stationary force plates may be provided. However, force plate arrays occupy a large amount of valuable building floor space, which could be used for other purposes. Instrumented treadmills are an alternative to force plate arrays. Although, instrumented treadmills have their own limitations and drawbacks. First of all, dual-belt instrumented treadmills are subject to leg crossing problems. Each of the belts of a dual-belt treadmill is designed to accommodate a single respective one of the subject's legs. However, during normal walking or running on an instrumented treadmill, subjects often cross their legs such that, for example, the right foot of the subject contacts the left belt of the instrumented treadmill and/or the left foot of the subject contacts the right belt of the instrumented treadmill. This leg crossing problem results in the acquisition of inaccurate gait data by the instrumented treadmill, which must be discarded. The test must then be repeated on the instrumented treadmill in order to acquire accurate gait data. In order to avoid the leg crossing problem, subjects sometimes modify their gait while walking or running on the instrumented treadmill, but this is not an appropriate remedy for the leg crossing problem because the self-imposed gait modifications result in an artificial gait data that does not reflect a subject's typical walking or running style.

Another limitation of conventional force measurement systems in the form of instrumented treadmills is associated with those systems that employ two separate belts (one behind the other) in the walking or running direction of the subject. In these systems, there is a transversely extending seam between the anterior and posterior belts that subject's feet often contact. Even if the width of this belt seam is greatly minimized, this belt seam can still interfere with the subject's normal gait pattern.

Therefore, what is needed is a force measurement system that employs a compact arrangement of force plates that is capable of accurately assessing the gait of a subject when the subject walks or runs on the force measurement system. Moreover, what is needed is a force measurement system that does not have the leg crossing problems associated with dual-belt instrumented treadmills. Furthermore, a force measurement system is needed that does not have the belt seam problems that are associated with instrumented treadmills having posteriorly and anteriorly located belts.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one or more embodiments of the present invention, there is provided a force measurement system having a plurality of force measurement assemblies arranged in a loop configuration, the plurality of force measurement assemblies configured to be displaced around a continuous path of movement such that a particular one of the plurality of force measurement assemblies that is disposed underneath a subject varies over time. Each of the plurality of force measurement assemblies includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject.

In a further embodiment of the present invention, each of the plurality of force measurement assemblies is attached to at least one continuous coupling member or assembly, the at least one continuous coupling member or assembly being configured to rotate about at least two spaced-apart, generally horizontal rotational axes.

In yet a further embodiment, when the plurality of force measurement assemblies are displaced around the continuous path of movement, each of the plurality of force measurement assemblies remains generally parallel to each other of the plurality of force measurement assemblies.

In still a further embodiment, when the plurality of force measurement assemblies are displaced around the continuous path of movement, each of the plurality of force measurement assemblies remains generally parallel to, or tangent to the at least one continuous coupling member or assembly.

In yet a further embodiment, the at least one continuous coupling member or assembly is guided over at least two spaced-apart rotary elements, each of the at least two spaced-apart rotary elements configured to rotate about a respective one of the at least two spaced-apart, generally horizontal rotational axes.

In still a further embodiment, each of the at least two spaced-apart rotary elements comprises one of: (i) a roller, (ii) a gear member, and (iii) a pulley.

In yet a further embodiment, as the plurality of force measurement assemblies are displaced around the continuous path of movement, an elevation of the top surfaces of each of the plurality of force measurement assemblies changes relative to a support surface on which the force measurement system is disposed.

In still a further embodiment, each of the plurality of force measurement assemblies is attached to at least one continuous coupling member or assembly, the at least one continuous coupling member or assembly being configured to rotate about at least two spaced-apart, generally vertical rotational axes.

In yet a further embodiment, at least one subset of the plurality of force measurement assemblies is arranged in a generally linear manner.

In still a further embodiment, at least two subsets of the plurality of force measurement assemblies are arranged in a generally linear manner.

In yet a further embodiment, a first of the at least two subsets of the plurality of force measurement assemblies is disposed generally parallel to a second of the at least two subsets of the plurality of force measurement assemblies.

In still a further embodiment, the loop configuration in which the plurality of force measurement assemblies is arranged comprises a plurality of curved end portions.

In yet a further embodiment, each of the plurality of curved end portions comprises a cover portion under which the force measurement assemblies pass as the force measurement assemblies are displaced around the continuous path of movement.

In still a further embodiment, as the plurality of force measurement assemblies are displaced around the continuous path of movement, the top surfaces of each of the plurality of force measurement assemblies remain at generally the same height relative to a support surface on which the force measurement system is disposed.

In yet a further embodiment, the plurality of force measurement assemblies are in the form of a plurality of force plates, and wherein a gap is provided between each of the plurality of force plates so as to prevent interaction between adjacent ones of the plurality of force plates.

In still a further embodiment, the force measurement system further comprises a data processing device operatively coupled to each of the force transducers of each of the force measurement assemblies, the data processing device configured to receive each of the one or more signals that are representative of the one or more measured quantities and to convert the one or more signals into load output data, the load output data comprising one or more forces and one or more moments.

In accordance with one or more other embodiments of the present invention, there is provided a force measurement system having a plurality of force measurement assemblies arranged in a loop configuration, the plurality of force measurement assemblies configured to be displaced around a continuous path of movement such that a particular one of the plurality of force measurement assemblies that is disposed underneath a subject varies over time. Each of the plurality of force measurement assemblies includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject. The force measurement system further comprises a data processing device operatively coupled to each of the force transducers of each of the force measurement assemblies, the data processing device configured to receive each of the one or more signals that are representative of the one or more measured quantities and to convert the one or more signals into load output data, the load output data comprising one or more forces and one or more moments.

In a further embodiment of the present invention, each of the plurality of force measurement assemblies is attached to at least one continuous coupling member or assembly, the at least one continuous coupling member or assembly being configured to rotate about at least two spaced-apart, generally horizontal rotational axes.

In yet a further embodiment, when the plurality of force measurement assemblies are displaced around the continuous path of movement, each of the plurality of force measurement assemblies remains generally parallel to each other of the plurality of force measurement assemblies.

In still a further embodiment, when the plurality of force measurement assemblies are displaced around the continuous path of movement, each of the plurality of force measurement assemblies remains generally parallel to, or tangent to the at least one continuous coupling member or assembly.

In yet a further embodiment, the at least one continuous coupling member or assembly is guided over at least two spaced-apart rotary elements, each of the at least two spaced-apart rotary elements configured to rotate about a respective one of the at least two spaced-apart, generally horizontal rotational axes.

In still a further embodiment, each of the at least two spaced-apart rotary elements comprises one of: (i) a roller, (ii) a gear member, and (iii) a pulley.

In yet a further embodiment, as the plurality of force measurement assemblies are displaced around the continuous path of movement, an elevation of the top surfaces of each of the plurality of force measurement assemblies changes relative to a support surface on which the force measurement system is disposed.

In still a further embodiment, each of the plurality of force measurement assemblies is attached to at least one continuous coupling member or assembly, the at least one continuous coupling member or assembly being configured to rotate about at least two spaced-apart, generally vertical rotational axes.

In yet a further embodiment, at least one subset of the plurality of force measurement assemblies is arranged in a generally linear manner.

In still a further embodiment, at least two subsets of the plurality of force measurement assemblies are arranged in a generally linear manner.

In yet a further embodiment, a first of the at least two subsets of the plurality of force measurement assemblies is disposed generally parallel to a second of the at least two subsets of the plurality of force measurement assemblies.

In still a further embodiment, the loop configuration in which the plurality of force measurement assemblies is arranged comprises a plurality of curved end portions.

In yet a further embodiment, each of the plurality of curved end portions comprises a cover portion under which the force measurement assemblies pass as the force measurement assemblies are displaced around the continuous path of movement.

In still a further embodiment, as the plurality of force measurement assemblies are displaced around the continuous path of movement, the top surfaces of each of the plurality of force measurement assemblies remain at generally the same height relative to a support surface on which the force measurement system is disposed.

In yet a further embodiment, the plurality of force measurement assemblies are in the form of a plurality of force plates, and wherein a gap is provided between each of the plurality of force plates so as to prevent interaction between adjacent ones of the plurality of force plates.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
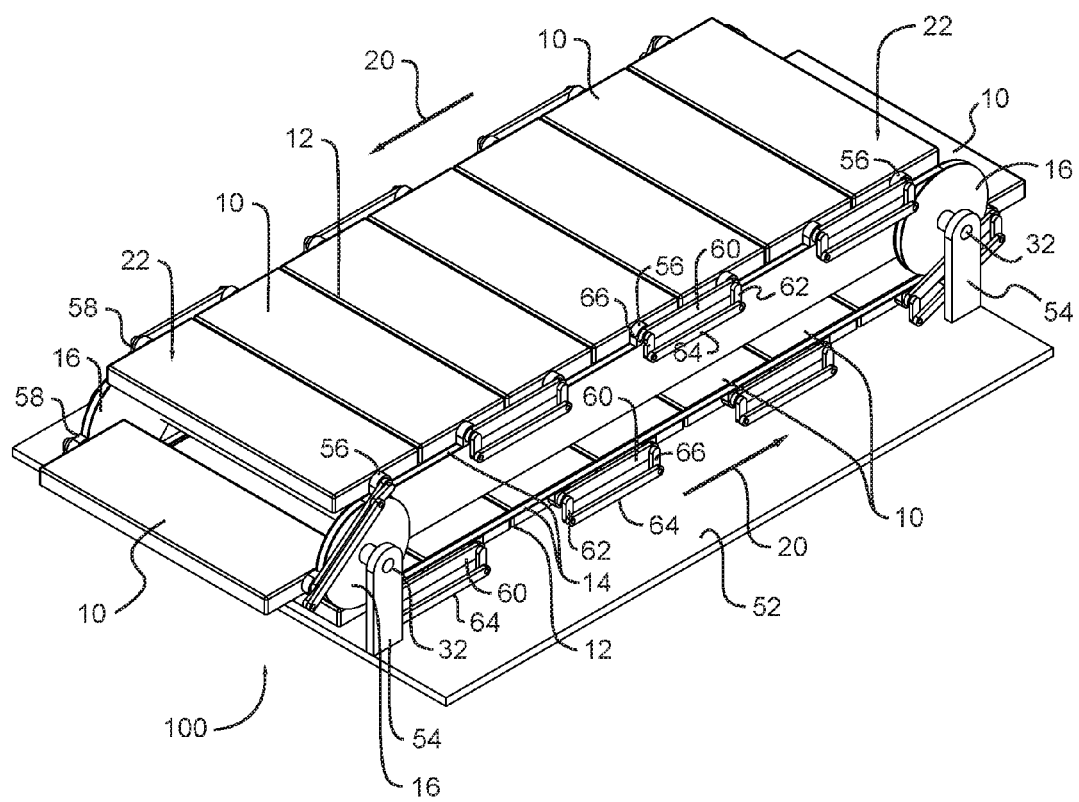
FIG. 1 is a perspective view of a force measurement system with a plurality of displaceable force plates arranged in a loop configuration, according to a first embodiment of the invention, wherein the force plates remain generally parallel to one another as they undergo displacement about a vertical loop.
Figure 2:
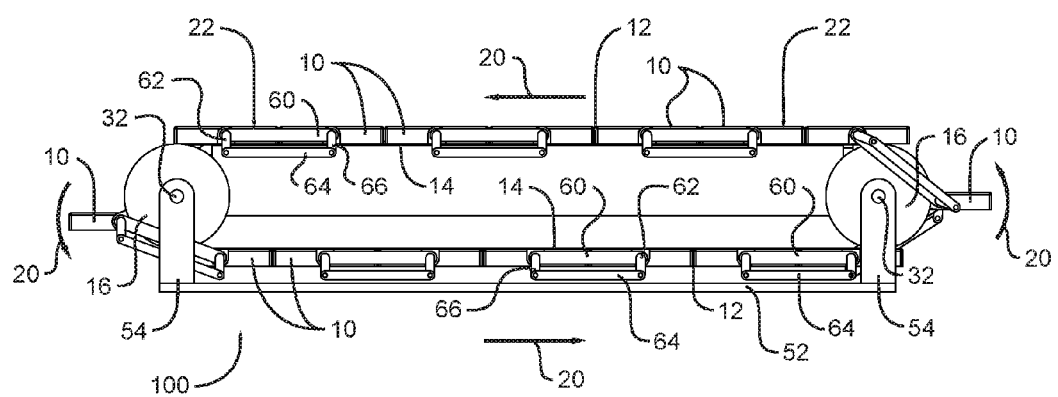
FIG. 2 is a side view of the force measurement system of FIG. 1.

A first embodiment of a force measurement system is seen generally at 100 in FIGS. 1 and 2. In the first illustrative embodiment, the force measurement system 100 generally comprises a plurality of force measurement assemblies 10 (i.e., force plates 10) arranged in a loop configuration (i.e., a vertical loop configuration wherein the loop is disposed in a vertical plane). The plurality of force measurement assemblies 10 of the force measurement system 100 are configured to receive a subject thereon. The plurality of force measurement assemblies 10 (i.e., force plates 10) are displaced around a continuous path of movement (as diagrammatically indicated by the displacement direction arrows 20 in FIGS. 1 and 2) such that a particular one of the plurality of force measurement assemblies 10 that is disposed underneath a subject varies over time. Each of the plurality of force measurement assemblies 10 (i.e., force plates 10) generally includes a top surface 22 for receiving at least one portion of the body of the subject, and a plurality of force transducers. As will be described in more detail hereinafter, the plurality of force transducers are configured to sense one or more measured quantities and output one or more signals that are representative of forces and/or moments being applied to the top surface 22 of each respective force measurement assembly 10 by the subject.

Figure 9:
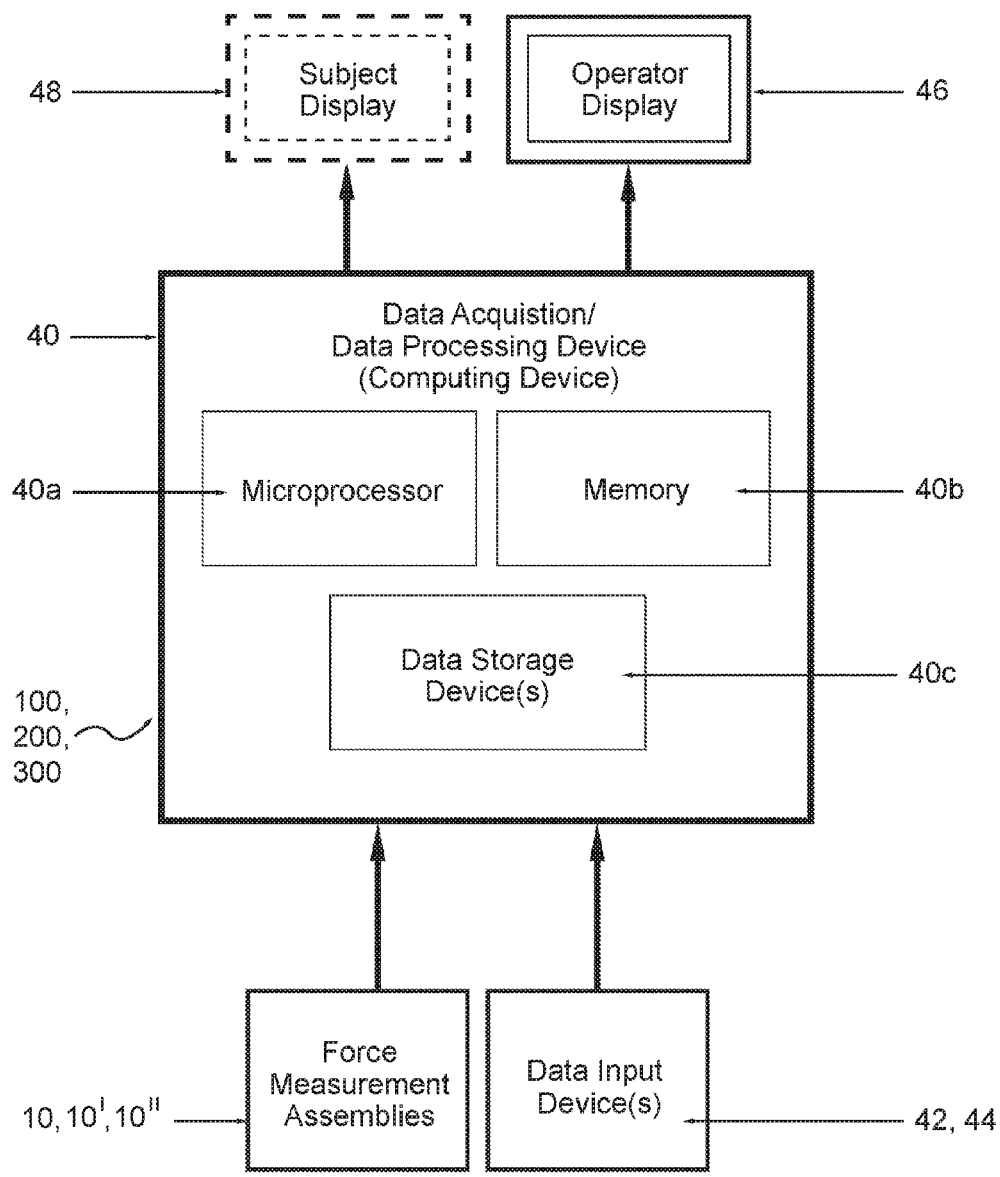
FIG. 9 is a block diagram of constituent components of the systems of FIGS. 1-6, according to an embodiment of the invention.

In one or more embodiments, a data acquisition/data processing device 40 (i.e., a data acquisition and processing device or computing device that is capable of collecting, storing, and processing data), is operatively coupled to each of the force transducers of each of the force measurement assemblies 10 (see FIG. 9). For example, each of the force measurement assemblies 10 may be wirelessly coupled to the data acquisition/data processing device 40 so that wires are not required to be routed from each of the force measurement assemblies 10 (i.e., each of the force measurement assemblies 10 may be assigned a unique identification number so that it may be easily identified in the wireless communications with the data acquisition/data processing device 40). As will be explained in more detail hereinafter, the data acquisition/data processing device 40 is configured to receive each of the one or more signals that are representative of the one or more measured quantities and to convert the one or more signals into load output data that comprises one or more forces and one or more moments.

In one or more embodiments, a subject walks or runs in an upright position atop one or more of the displaceable force measurement assemblies 10 of the force measurement system 100. Referring again to FIGS. 1 and 2, it can be seen that each of the plurality of force measurement assemblies 10 (i.e., force plates 10) are attached to a spaced-apart pair of continuous coupling members 14 that, in conjunction with linkage assemblies described hereinafter, connect the force measurement assemblies 10 to one another such that the force measurement assemblies 10 are capable of being rotated together. As shown in the illustrative embodiment of FIGS. 1 and 2, each continuous coupling member 14 rotates about two spaced-apart, generally horizontal rotational axes 32 (e.g., as formed by the rotating pins of friction wheels 16). In one or more embodiments, each continuous coupling member 14 may comprise an endless belt to which each of the force measurement assemblies 10 is attached. In one or more other embodiments, the plurality of force measurement assemblies 10 may be displaced around a continuous track or tracks. For example, tracks may be provided on each side of the force measurement assemblies 10, and each of the force measurement assemblies 10 may be provided with opposed protruding members that engage each of the respective tracks.

Turning to FIG. 2, it can be seen that, when the plurality of force measurement assemblies 10 are displaced around the continuous path of movement, each of the plurality of force measurement assemblies 10 remains generally parallel to each other of the plurality of force measurement assemblies (i.e., the top surfaces 22 of the force plates 10 remain generally parallel to one another as the force plates 10 are displaced around the continuous path of movement). Also, as the plurality of force measurement assemblies 10 are displaced around the continuous path of movement, an elevation of the top surfaces 22 of each of the plurality of force measurement assemblies 10 changes relative to a support surface (e.g., the building floor) on which the force measurement system 100 is disposed. In particular, with reference to FIGS. 1 and 2, the force measurement assemblies 10 that are displaced along the bottom linear portion of the loop are generally at the same first elevation, and the force measurement assemblies 10 displaced along the top linear portion of the loop are generally at the same second elevation, which is greater than the first elevation. However, when each of the force measurement assemblies 10 reaches the opposed end portions of the force measurement system 100, the elevation of the force measurement assemblies 10 changes relative to a support surface (e.g., the building floor) on which the force measurement system 100 is disposed (i.e., each force measurement assembly 10 ascends in elevation at the first end of the force measurement system 100, and then descends in elevation at the second, opposite end of the force measurement system 100.

Referring again to the first illustrative embodiment of FIGS. 1 and 2, it can be seen that each of the transversely spaced-apart pair of continuous coupling members 14 is guided over a pair of longitudinally spaced-apart rotary elements (e.g., friction wheels 16). Each of the spaced-apart friction wheels 16 is configured to rotate about a respective one of the longitudinally spaced-apart, generally horizontal rotational axes 32. In one or more embodiments, each of the spaced-apart friction wheels may comprise one of: (i) a roller, (ii) a gear member, (iii) a pulley, and (iv) a sheave. For example, in the illustrative embodiment of FIGS. 1 and 2, each friction wheel 16 comprises a pulley or sheave with a circumferential groove formed therein for receiving and engaging a respective one of the continuous coupling members 14. Also, it can be seen that, in the illustrative embodiment of FIGS. 1 and 2, each friction wheel 16 comprises a centrally disposed pin that rotates within an aperture of a stationary support post member 54. That is, each friction wheel 16 rotates relative to its stationary support post member 54. As best shown in the perspective view of FIG. 1, each of the plurality of support post member 54 (i.e., each of the four (4) support post members 54) is affixedly attached to a base member 52 (e.g., a base plate) that extends underneath the force measurement system 100. In one or more embodiments, each friction wheel 16 may be in the form of a pulley or sheave and each continuous coupling member 14 may be in the form of an endless belt that frictionally engages each pulley or sheave, and is disposed within the circumferential groove of each pulley or sheave. Each continuous coupling member 14 may be rotated by one or both of the friction wheels 16 with which it is engaged (i.e., one or both of the friction wheels 16 on each side may be driving wheels). In turn, one or more of the plurality of friction wheels 16 (e.g., four (4) friction wheels 16) may be rotated by an electric actuator assembly with a speed adjustment mechanism. In one or more embodiments, the electric actuator assembly and associated speed adjustment mechanism comprises an electric motor with a variable speed control device operatively coupled thereto. The electric actuator assembly and associated speed adjustment mechanism is capable of rotating one or more of the friction wheels 16 at a plurality of different speeds. The speed adjustment mechanism allows the speed at which the continuous coupling member 14, and the force measurement assemblies 10 attached thereto, to be selectively adjusted by a user of the force measurement system 100.

With combined reference to FIGS. 1 and 2, the linkage assemblies (with constituent members 60, 62, 64, 66) that connect adjacent force measurement assemblies 10 to one another will now be described. Initially, referring to the perspective view of FIG. 1, it can be seen that each of the force measurement assemblies 10 (i.e., force plates) of the force measurement system 100 is connected to each of the two force measurement assemblies 10 disposed on its opposite sides. More particularly, one end of each force measurement assembly 10 is coupled to the force measurement assembly 10 immediately behind the force measurement assembly 10 in succession, while the other, opposite end of each force measurement assembly 10 is coupled to the force measurement assembly 10 immediately in front of the force measurement assembly 10 in succession (refer to FIG. 1). As such, the linkage assemblies on the opposite sides of the force measurement system 100 are disposed in a staggered manner relative to one another (i.e., the linkage assemblies on one side of the force measurement system 100 are offset with respect to the linkage assemblies on the other side of the force measurement system 100 such that no two of the linkage assemblies couple the same two force measurement assemblies 10 to one another).

Referring again to FIGS. 1 and 2, it can be seen that each of the linkage assemblies is generally in the form of a four-bar linkage system with a first linkage member 60, a second linkage member 62, a third linkage member 64, and a fourth linkage member 66. As shown in these figures, each of the two opposed ends of each force measurement assembly 10 comprises a shaft 58 extending outwardly therefrom. In the illustrative embodiment of FIGS. 1 and 2, each shaft 58 is affixedly secured to its respective end of the respective force measurement assembly 10 so that the shaft 58 is stationary relative to the force measurement assembly 10. As such, the pair of shafts 58 on each force measurement assembly 10 are not displaced relative to the force measurement assembly 10. Turning again to FIGS. 1 and 2, it can be seen that, for each coupled pair of adjacent force measurement assemblies 10, the shaft 58 of one of the force measurement assemblies 10 is affixedly attached to the second linkage member 62, while the shaft 58 of the other of the force measurement assemblies 10 is affixedly attached to the fourth linkage member 66 such that the second and fourth linkage members 62, 66 rotate together with each of their respective shafts 58. The second and fourth linkage members 62, 66 are rotatably coupled to one another by the third linkage member 64. That is, the third linkage member 64 rotates relative to both of the second and fourth linkage members 62, 66 as the force measurement assemblies 10 are displaced around their continuous path of movement. In one or more embodiments, the opposed ends of the third linkage member 64 may be rotatably coupled to a respective one of the second and fourth linkage members 62, 66 by a respective pin member. In the illustrative embodiment, for added stability during rotation, the first linkage member 60 of each linkage assembly is also rotatably coupled to the shafts 58 of the coupled pair of adjacent force measurement assemblies 10 (i.e., like the third linkage member 64, the first linkage member 60 rotates relative to the force measurement assembly shafts 58 as the force measurement assemblies 10 are displaced around their continuous path of movement. Referring again to FIG. 1, it can be seen that the shafts 58, which are affixed to the opposed ends of each force measurement assembly 10, are rotatably coupled to the continuous coupling members 14 by respective bearing members 56 (i.e., by respective roller bearing members or ball bearing members). Thus, as each of the force measurement assemblies 10 is displaced along the continuous path of movement by the continuous coupling members 14, the shafts 58 of each force measurement assembly 10 rotate within their respective bearing members 56.

As shown in FIGS. 1 and 2, the force measurement assemblies 10, which are in the form of force plates 10 in the illustrative embodiment, are separated from one another by narrow gaps 12. That is, in the illustrative embodiment, a narrow gap 12 is provided between each of the plurality of force plates 10 so as to prevent interaction between adjacent ones of the plurality of force plates 10. In an exemplary embodiment, the narrow gap 12 between adjacent force plates 10 may be between approximately 2 mm and approximately 3 mm (or between 2 mm and 3 mm). As best shown in FIG. 1, the narrow gap 12 is continuous, and extends the full width of the force measurement assembly 100, in order to completely separate adjacent force plates 10 from one another. (i.e., the adjacent force plates 10 do not contact one another at any location along the gap 12).

Figure 3:
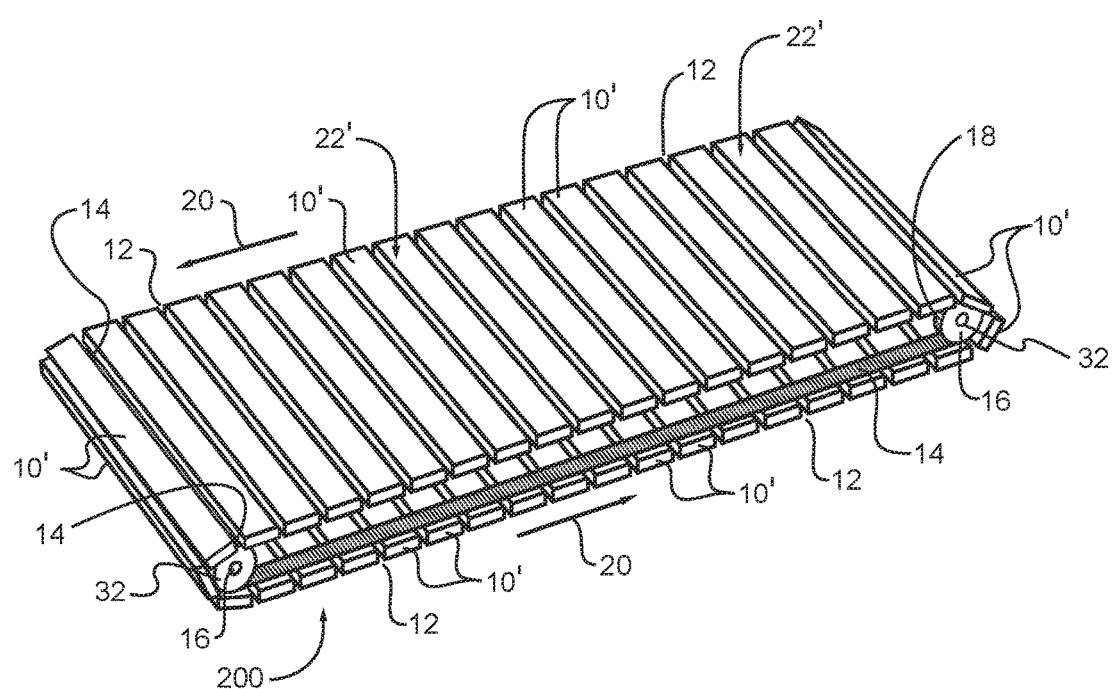
FIG. 3 is a perspective view of a force measurement system with a plurality of displaceable force plates arranged in a loop configuration, according to a second embodiment of the invention, wherein the force plates remain generally parallel to, or tangent to the continuous coupling member to which they are attached as they undergo displacement about a vertical loop.
Figure 4:
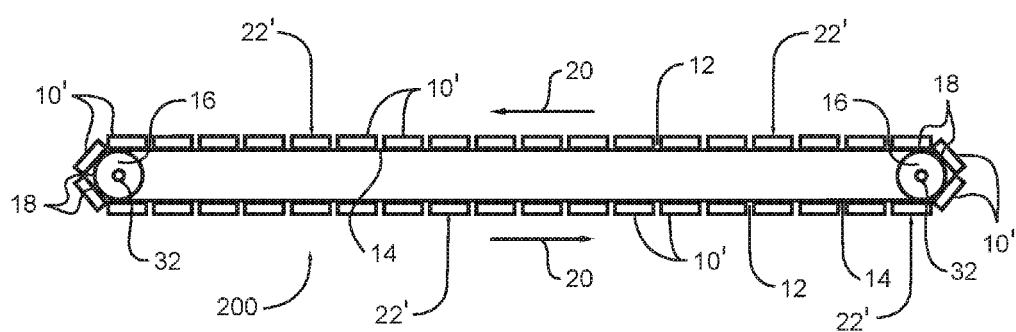
FIG. 4 is a side view of the force measurement system of FIG. 3.

A second embodiment of the force measurement system is seen generally at 200 in FIGS. 3 and 4. With reference to these figures, it can be seen that the force measurement system 200 is similar in some respects to the force measurement system 100 of the first embodiment described above. Similar to the aforedescribed first embodiment, the force measurement system 200 generally comprises a plurality of force measurement assemblies 10' (i.e., force plates 10') arranged in a loop configuration (i.e., a vertical loop configuration wherein the loop is disposed in a vertical plane). The plurality of force measurement assemblies 10' (i.e., force plates 10') are displaced around a continuous path of movement (as diagrammatically indicated by the displacement direction arrows 20 in FIGS. 3 and 4) such that a particular one of the plurality of force measurement assemblies 10' that is disposed underneath a subject varies over time. Each of the plurality of force measurement assemblies 10' (i.e., force plates 10') generally includes a top surface 22' for receiving at least one portion of the body of the subject, and a plurality of force transducers configured to sense one or more measured quantities and output one or more signals that are representative of forces and/or moments being applied to the top surface 22' of each respective force measurement assembly 10' by the subject.

Also, as explained above for the force measurement system 100, each of the force transducers of each of the force measurement assemblies 10' of the force measurement system 200 may be operatively coupled to the data acquisition/data processing device 40 (i.e., a data acquisition and processing device or computing device that is capable of collecting, storing, and processing data). For example, each of the force measurement assemblies 10' may be wirelessly coupled to the data acquisition/data processing device 40 so that wires are not required to be routed from each of the force measurement assemblies 10' (i.e., each of the force measurement assemblies 10' may be assigned a unique identification number so that it may be easily identified in the wireless communications with the data acquisition/data processing device 40). In addition, referring again to FIGS. 3 and 4, it can be seen that each of the plurality of force measurement assemblies 10' (i.e., force plates 10') are attached to a pair of transversely spaced-apart continuous coupling members 14 that connect the force measurement assemblies 10' to one another such that the force measurement assemblies 10' are capable of being rotated together. As in the first embodiment of FIGS. 1 and 2, each of the pair of continuous coupling members 14 rotates about a pair of longitudinally spaced-apart, generally horizontal rotational axes 32.

However, unlike the aforedescribed force measurement system 100, when the plurality of force measurement assemblies 10' of the force measurement system 200 are displaced around the continuous path of movement, each of the plurality of force measurement assemblies 10' remains generally parallel to, or tangent to the continuous coupling member 14 (see FIG. 4), rather than remaining generally parallel to one another as in the first embodiment. Referring to FIGS. 3 and 4, it can be seen that, as the plurality of force measurement assemblies 10' are displaced around the continuous path of movement, an elevation of the top surfaces 22' of each of the plurality of force measurement assemblies 10' changes relative to a support surface (e.g., the building floor) on which the force measurement system 200 is disposed. In particular, with reference to FIGS. 3 and 4, the force measurement assemblies 10' that are displaced along the bottom linear portion of the loop are generally at the same first elevation, and the force measurement assemblies 10' displaced along the top linear portion of the loop are generally at the same second elevation, which is greater than the first elevation. However, when each of the force measurement assemblies 10' reaches the opposed end portions of the force measurement system 200, the elevation of the force measurement assemblies 10' changes relative to a support surface (e.g., the building floor) on which the force measurement system 200 is disposed (i.e., each force measurement assembly 10' ascends in elevation at the first end of the force measurement system 200, and then descends in elevation at the second, opposite end of the force measurement system 200). When the force measurement assemblies 10' are displaced along the bottom and top linear portions of the loop, each of the plurality of force measurement assemblies 10' remains generally parallel to the continuous coupling member 14, whereas, when the force measurement assemblies 10' are displaced along the opposed end portions of the loop, each of the plurality of force measurement assemblies 10' remains generally tangent to the continuous coupling member 14.

Referring again to FIGS. 3 and 4, it can be seen that each of the pair of continuous coupling members 14 of the second embodiment is engaged with a respective pair of longitudinally spaced-apart friction wheels 16 comprising a plurality of teeth or grooves 18 circumferentially spaced apart about the periphery thereof. In particular, each continuous coupling member 14, which may be in the form of an endless belt, is engaged with the teeth or grooves 18 of each friction wheel 16 so that the continuous coupling member 14 rotates with its respective pair of friction wheels 16 (e.g., to prevent slippage, the continuous coupling member 14 may comprise grooves that correspond to, and interlock with, the teeth or grooves 18 of the friction wheels 16). Similar to the first embodiment, each of the spaced-apart friction wheels 16 is configured to rotate about a respective one of the two spaced-apart, generally horizontal rotational axes 32. Also, in the second embodiment, the friction wheels 16 are driven in the same manner as that described above for the first illustrative embodiment. In addition, as shown in FIGS. 3 and 4, the force measurement assemblies 10' (i.e., the force plates 10') of the second embodiment are separated from one another by narrow gaps 12 similar to those described above in conjunction with the first embodiment.

Figure 5:
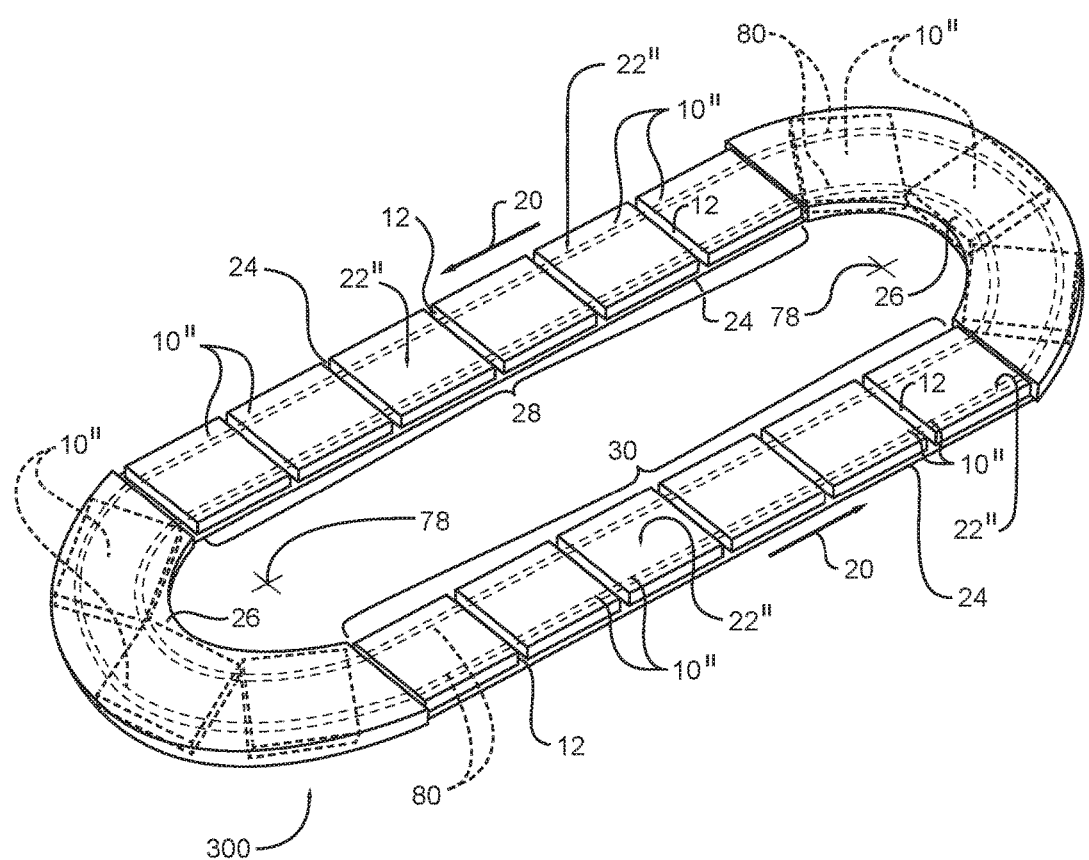
FIG. 5 is a perspective view of a force measurement system with a plurality of displaceable force plates arranged in a loop configuration, according to a third embodiment of the invention, wherein the force plates are displaced about a horizontal loop.
Figure 6:
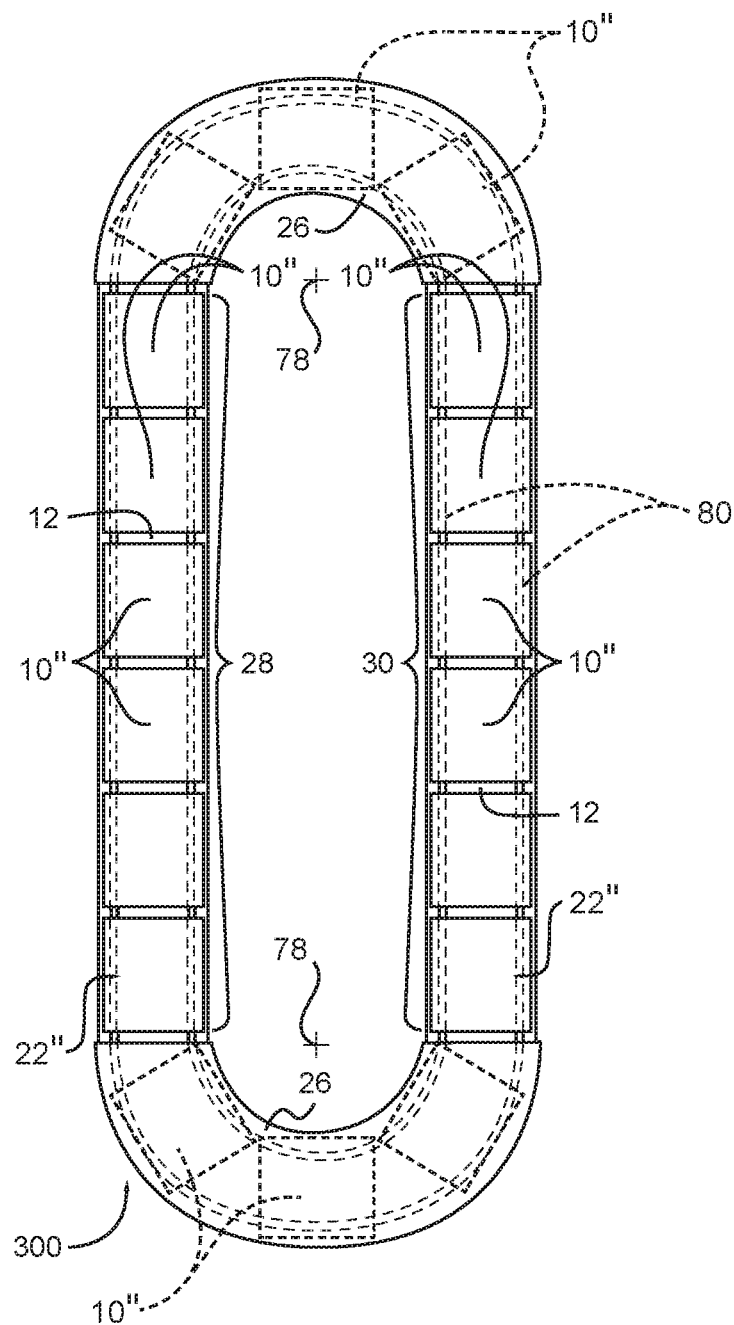
FIG. 6 is a top view of the force measurement system of FIG. 5.

A third embodiment of a force measurement system is seen generally at 300 in FIGS. 5 and 6. With reference to these figures, it can be seen that the force measurement system 300 is similar in some respects to the force measurement systems 100, 200 of the first and second embodiments described above. Similar to the aforedescribed embodiments, the force measurement system 300 generally comprises a plurality of force measurement assemblies 10" (i.e., force plates 10") arranged in a loop configuration. However, unlike the preceding two embodiments, the force measurement assemblies 10" (i.e., force plates 10") of the third embodiment are arranged in a horizontal loop configuration wherein the loop is disposed in a horizontal plane. The plurality of force measurement assemblies 10" of the force measurement system 300 are configured to receive one or more subjects thereon. For example, as shown in FIGS. 5 and 6, the force measurement system 300 may comprise a first subject testing portion 28 for receiving a first subject and a second subject testing portion 30 for receiving a second subject so that two subjects may be tested simultaneously on the force measurement system 300. With reference to the perspective view of FIG. 5, it can be seen that the plurality of force measurement assemblies 10" (i.e., force plates 10") are displaced around a continuous path of movement (as diagrammatically indicated by the displacement direction arrows 20 in FIG. 5) such that a particular one of the plurality of force measurement assemblies 10" that is disposed underneath the one or more subjects varies over time. Each of the plurality of force measurement assemblies 10" (i.e., force plates 10") generally includes a top surface 22" for receiving at least one portion of the body of the subject, and a plurality of force transducers. As will be described in more detail hereinafter, the plurality of force transducers are configured to sense one or more measured quantities and output one or more signals that are representative of forces and/or moments being applied to the top surface 22" of each respective force measurement assembly 10" by the one or more subjects. Also, as shown in FIGS. 5 and 6, the force measurement assemblies 10" (i.e., the force plates 10") of the third embodiment are separated from one another by narrow gaps 12 similar to those described above in conjunction with the first and second embodiments.

As explained above for the force measurement systems 100, 200, each of the force transducers of each of the force measurement assemblies 10" of the force measurement system 300 may be operatively coupled to the data acquisition/data processing device 40 (i.e., a data acquisition and processing device or computing device that is capable of collecting, storing, and processing data). For example, each of the force measurement assemblies 10" may be wirelessly coupled to the data acquisition/data processing device 40 so that wires are not required to be routed from each of the force measurement assemblies 10" (i.e., each of the force measurement assemblies 10" may be assigned a unique identification number so that it may be easily identified in the wireless communications with the data acquisition/data processing device 40). In addition, similar to that described above for the preceding two embodiments, each of the plurality of force measurement assemblies 10" (i.e., force plates 10") may be attached to a continuous coupling member that connects the force measurement assemblies 10" to one another such that the force measurement assemblies 10" are capable of being rotated together. In the third illustrative embodiment, the continuous coupling member rotates about at least two spaced-apart, generally vertical rotational axes 78 (i.e., two imaginary spaced-apart, generally vertical rotational axes 78). In one or more embodiments, the continuous coupling member may comprise an endless belt to which each of the force measurement assemblies 10" is attached. In one or more other embodiments, the plurality of force measurement assemblies 10" may be displaced around a continuous track or tracks 80. For example, tracks 80 may be provided on each side of the force measurement assemblies 10" (see FIGS. 5 and 6), and each of the force measurement assemblies 10" may be provided with protruding members that engage each of the respective tracks 80. In the third illustrative embodiment, the force measurement assemblies 10" are supported on a base 24, which may be disposed directly on the support surface (e.g., the building floor).

In FIG. 5, it can be seen that, when the plurality of force measurement assemblies 10" are displaced around the continuous path of movement, each of the plurality of force measurement assemblies 10" remains generally parallel to each other of the plurality of force measurement assemblies (i.e., the top surfaces 22" of the force plates 10" remain generally parallel to one another as the force plates 10" are displaced around the continuous path of movement). Also, as the plurality of force measurement assemblies 10" are displaced around the continuous path of movement, the top surfaces 22" of each of the plurality of force measurement assemblies 10" remain at generally the same height relative to a support surface (e.g., the building floor) on which the force measurement system 300 is disposed. In FIGS. 5 and 6, it can be seen that the first subject testing portion 28 comprises a first subset of force measurement assemblies 10" are arranged in a generally linear manner (e.g., a linear arrangement of six (6) force measurement assemblies 10"), while the second subject testing portion 30 comprises a second subset of force measurement assemblies 10" are arranged in a generally linear manner (e.g., a linear arrangement of six (6) force measurement assemblies 10"). As best shown in the top view of FIG. 6, the first subset of force measurement assemblies 10" is disposed generally parallel to the second subset of force measurement assemblies 10". With combined reference to FIGS. 5 and 6, it can be seen that, in the third illustrative embodiment, the horizontal loop configuration in which the plurality of force measurement assemblies 10" is arranged comprises a plurality of curved end portions with end cover portions 26 under which the force measurement assemblies 10" pass as the force measurement assemblies 10" are displaced around the continuous horizontal path of movement. Advantageously, the oppositely disposed cover portions 26 of the force measurement system 300 result in the force measurement system 300 having a more finished appearance because these covers 26 conceal the force measurement assemblies 10" thereunder as the force measurement assemblies 10" are displaced about the curved end portions of the force measurement system 300.

Similar to that described above for the first and second embodiments, the continuous coupling member of the third embodiment may also be driven by a plurality of friction wheels with a plurality of teeth or grooves circumferentially spaced apart about the periphery thereof. In one or more embodiments, each of the friction wheels may comprise one of: (i) a roller, (ii) a gear member, (iii) a pulley, and (iv) a sheave. Also, in one or more embodiments, each friction wheel may be in the form of a roller or pulley and the continuous coupling member may be in the form of an endless belt that frictionally engages each roller or pulley. The continuous coupling member of the third embodiment may be rotated by a plurality of friction wheels, which operate as driving wheels. In turn, the plurality of friction wheels may be rotated by electric actuator assemblies with one or more speed adjustment mechanisms. In one or more embodiments, the electric actuator assemblies and associated speed adjustment mechanisms comprise electric motors with one or more variable speed control devices operatively coupled thereto. The electric actuator assemblies and associated speed adjustment mechanisms are capable of rotating the friction wheels at a plurality of different speeds. The speed adjustment mechanisms allow the speed at which the continuous coupling member, and the force measurement assemblies 10" attached thereto, to be selectively adjusted by a user of the force measurement system 300.

Figure 7:
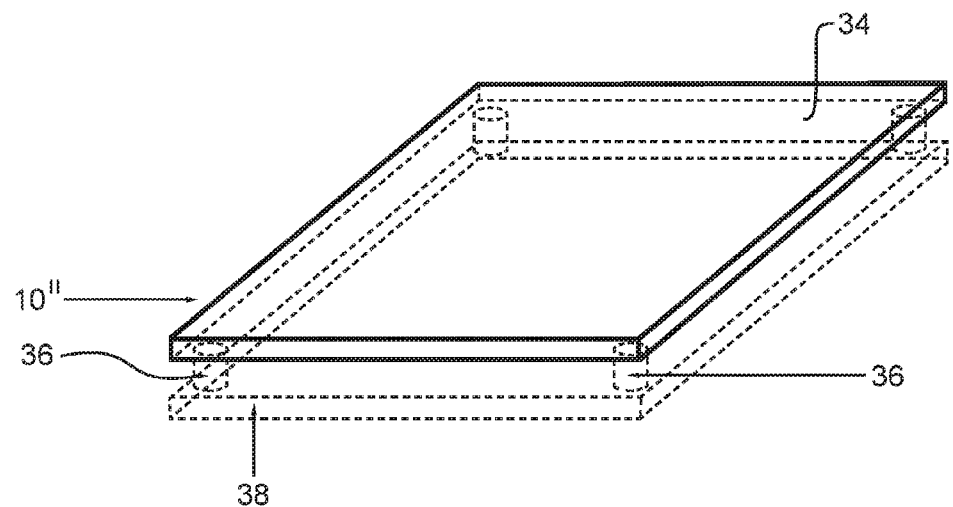
FIG. 7 is a diagrammatic perspective view of a force measurement assembly used in the force measurement system of FIGS. 5 and 6, according to an embodiment of the invention.

Now, with reference to FIGS. 7 and 8, the structural details of force measurement assemblies 10" that may be utilized in conjunction with the force measurement system 300 will be described. In the illustrated embodiment of FIGS. 7 and 8, wherein the side plates of the force measurement assembly 10" have been removed, it can be seen that each force measurement assembly 10" (i.e., force plate 10") comprises a top plate 34 supported atop a plurality of pylon-type force transducers 36 (i.e., four (4) pylon-type load cells 36). In particular, as shown in FIG. 7, the plurality of pylon-type force transducers 36 (i.e., four (4) pylon-type load cells 36) are disposed underneath, and near each of the four corners (4) of the top plate 34 of each force measurement assembly 10". Each of the plurality of pylon-type force transducers 36 may have a plurality of strain gages adhered to the outer periphery of a cylindrically-shaped force transducer sensing element for detecting the mechanical strain of the force transducer sensing element imparted thereon by the force(s) applied to the top surface 22" of the force measurement assembly 10" by the subject (e.g., as described in U.S. Pat. No. 6,354,155, the entire disclosure of which is incorporated herein by reference). As shown in FIG. 7, a base plate 38 may be provided underneath the transducers 36 of each force measurement assembly 10". In some embodiments, side plates are mounted between the base plate 38 and the top plate 34 so as to conceal the force transducers 36 (e.g., as shown in FIGS. 5 and 6).

In an alternative embodiment, rather than using four (4) pylon-type force transducers 36 on each force measurement assembly 10", force transducers in the form of transducer beams could be provided under each top plate 34 (e.g., as will be described in conjunction with FIGS. 11-14 below). In this alternative embodiment, the top plate 34 may comprise two transducer beams that are disposed underneath, and on generally opposite sides or ends of the top plate 34. Similar to the pylon-type force transducers 36, the force transducer beams could have a plurality of strain gages attached to one or more surfaces thereof for sensing the mechanical strain imparted on the beam by the force(s) applied to the surface (s) of the force measurement assembly 10".

While illustrative embodiment of the force measurement assembly 10" in FIG. 7 has been described in conjunction with the third embodiment, it is to be understood that the aforedescribed structural configuration of the force plate in FIG. 7 is equally applicable to the first and second embodiments as well. That is, the force measurement assemblies 10, 10' utilized in the first and second illustrative embodiments are generally the same as that depicted in FIG. 7, except that the force measurement assemblies 10, 10' of these embodiments are generally narrower in width.

Figure 11:
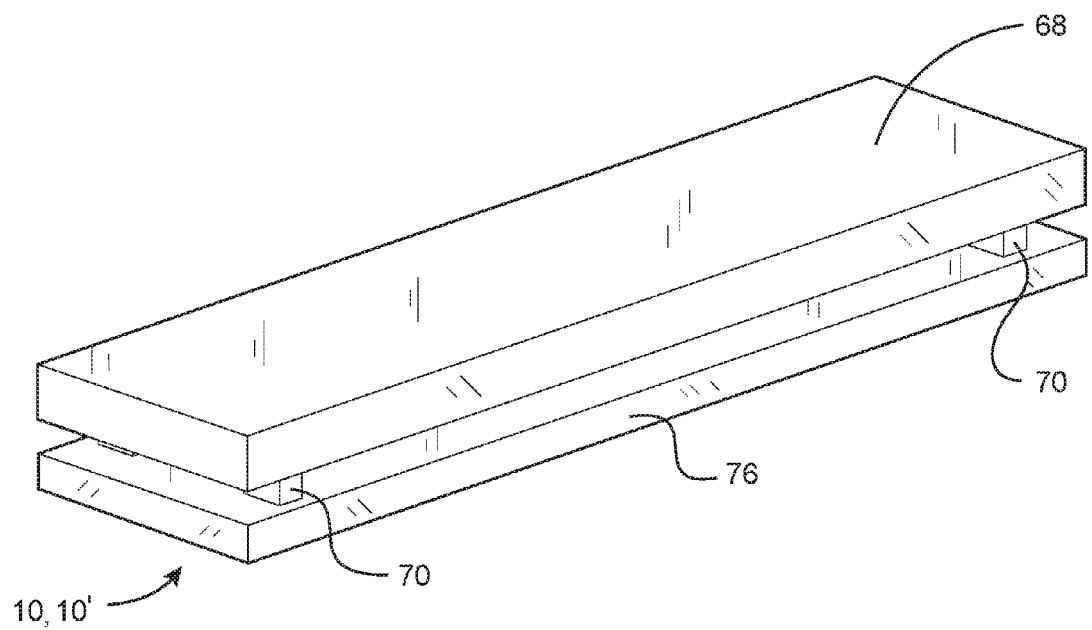
FIG. 11 is a perspective view of a force measurement assembly used in the force measurement systems of FIGS. 1-2 and 3-4, according to another embodiment of the invention.
Figure 12:
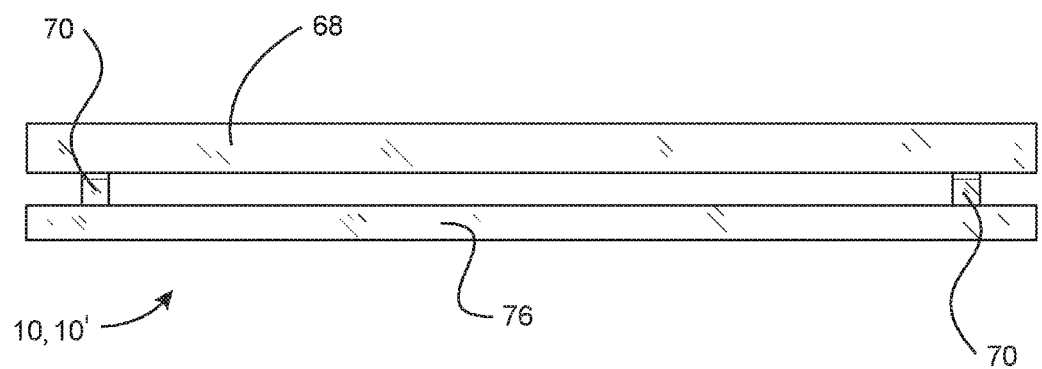
FIG. 12 is a side view of the force measurement assembly of FIG. 11.
Figure 13:
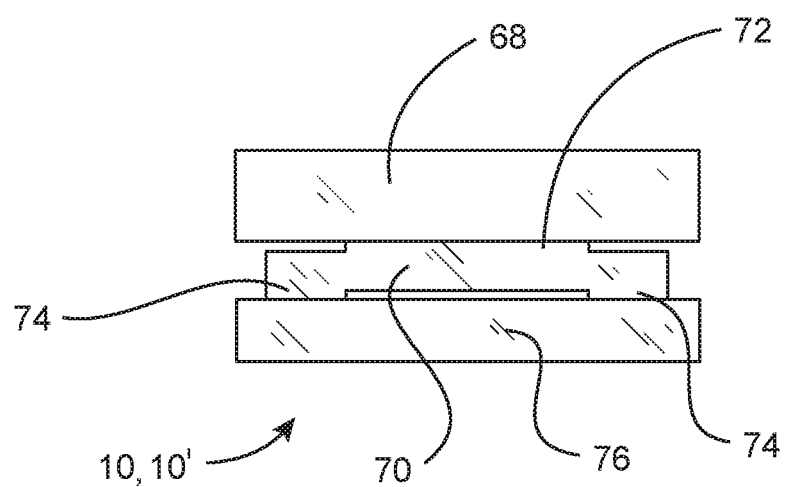
FIG. 13 is an end view of the force measurement assembly of FIG. 11.
Figure 14:
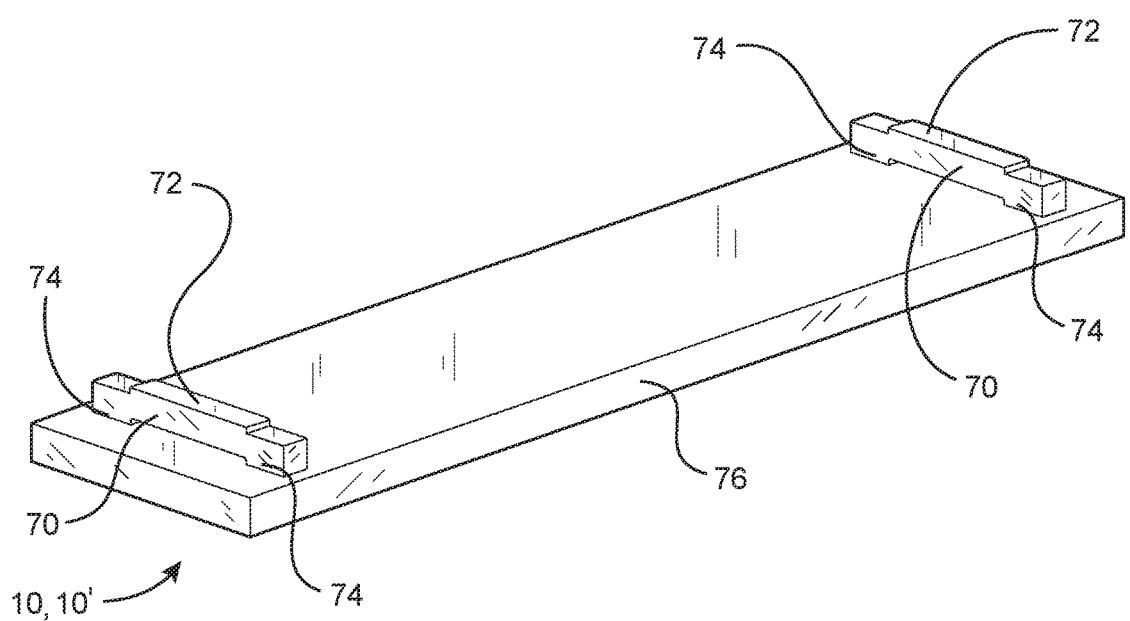
FIG. 14 is another perspective view of the force measurement assembly of FIG. 11, wherein the top plate has been removed from the force measurement assembly in order to better illustrate the force transducer beams at the opposed ends of the force measurement assembly.

Next, with reference to FIGS. 11-14, the structural details of force measurement assemblies 10, 10' that may be utilized in conjunction with the force measurement systems 100, 200 will be described. In the illustrated embodiment of FIGS. 11-14, wherein the side plates of the force measurement assembly 10, 10' have been removed, it can be seen that, each force measurement assembly 10, 10' (i.e., force plate 10, 10') comprises a top plate 68 supported atop a plurality of force transducer beams 70 (i.e., two (2) force transducer beams 70). In particular, as shown in FIGS. 11, 12, and 14, the plurality of force transducer beams 70 (i.e., two (2) force transducer beams 70) are disposed underneath, and near each of the respective oppositely disposed ends of the top plate 68 of each force measurement assembly 10, 10'. As best shown in FIGS. 13 and 14, each of the force transducer beams 70 has a top standoff portion 72 attached to the top plate 68 and bottom standoff portions 74 attached to a base plate 76. Each of the plurality of force transducer beams 70 may have a plurality of strain gages adhered to an outer surface of the beam-shaped force transducer sensing element for detecting the mechanical strain of the force transducer sensing element imparted thereon by the force(s) applied to the top surface 22, 22' of the force measurement assembly 10, 10' by the subject. As shown in FIGS. 11-14, the base plate 76 may be provided underneath the force transducer beams 70 of each force measurement assembly 10, 10'. In some embodiments, side plates are mounted between the base plate 76 and the top plate 68 so as to conceal the force transducer beams 70 (e.g., as shown in FIGS. 1-2 and 3-4).

In an alternative embodiment, rather than using the pair of force transducer beams 70 on each force measurement assembly 10, 10', force transducers in the form of pylon-type force transducers could be provided under each top plate 68 (e.g., the four (4) pylon-type force transducers 36 described above in conjunction with FIGS. 7 and 8).

While illustrative embodiment of the force measurement assembly 10, 10' in FIGS. 11-14 has been described in conjunction with the first and second embodiments, it is to be understood that the aforedescribed structural configuration of the force plate in FIGS. 11-14 is equally applicable to the third embodiments as well. That is, the force measurement assemblies 10" utilized in the third illustrative embodiment may be generally the same as that depicted in FIGS. 11-14, except that the force measurement assemblies 10" of this embodiment are generally wider than in the first two embodiments.

Now, turning to FIG. 9, it can be seen that the illustrated data acquisition/data processing device 40 (i.e., the operator computing device) of the force measurement systems 100, 200, 300 includes a microprocessor 40a for processing data, memory 40b (e.g., random access memory or RAM) for storing data during the processing thereof, and data storage device(s) 40c, such as one or more hard drives, compact disk drives, floppy disk drives, flash drives, or any combination thereof. As shown in FIG. 9, the force measurement assemblies 10, 10', 10" and the operator visual display device 46 are operatively coupled to the data acquisition/data processing device 40 such that data is capable of being transferred between these devices 10, 10', 10", 40, and 46. Also, as illustrated in FIG. 9, a plurality of data input devices 42, 44, such as a keyboard and mouse, are diagrammatically shown in FIG. 9 as being operatively coupled to the data acquisition/data processing device 40 so that a user is able to enter data into the data acquisition/data processing device 40. Also, as shown in FIG. 9, the force measurement systems 100, 200, 300 may also include a dedicated subject visual display device 48 for displaying images to the subject disposed on the force measurement assemblies 10, 10', 10". In some embodiments, the data acquisition/data processing device 40 can be in the form of a desktop computer, while in other embodiments, the data acquisition/data processing device 40 can be embodied as a laptop computer.

Figure 8:
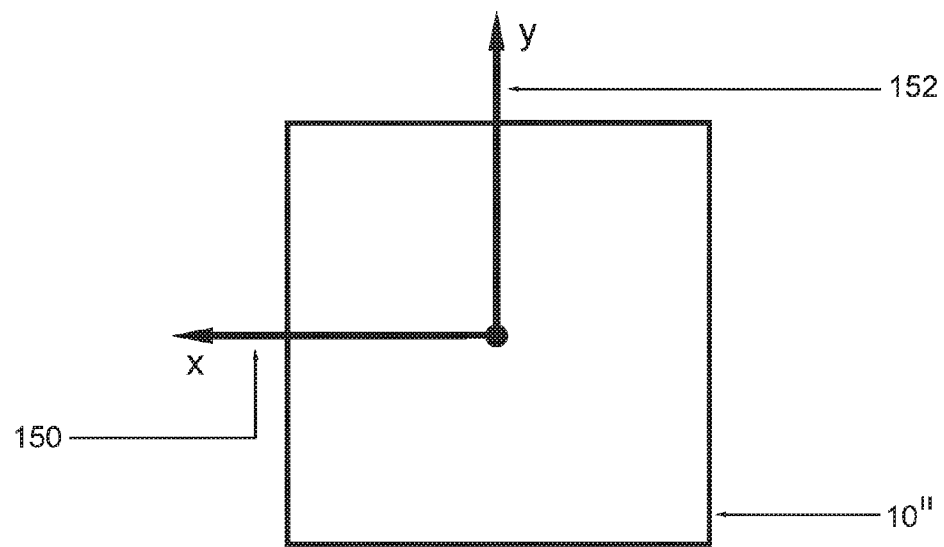
FIG. 8 is a diagrammatic top view of the measurement assembly used in the force measurement system of FIGS. 5 and 6 with exemplary coordinate axes superimposed thereon, according to an embodiment of the invention.
Figure 10:
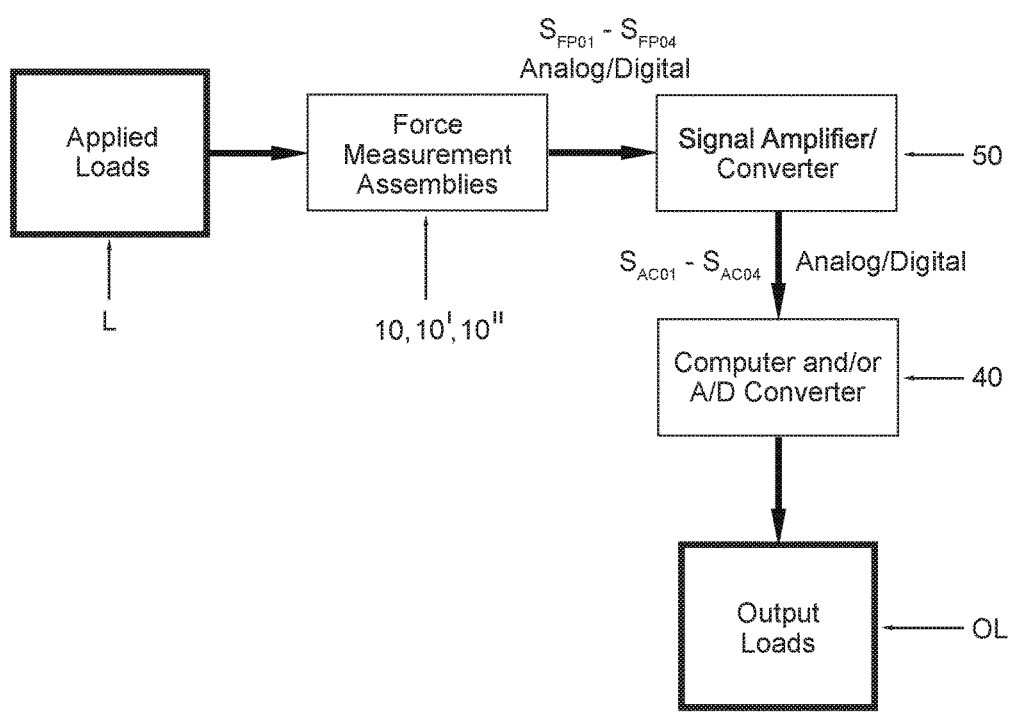
FIG. 10 is a block diagram illustrating data manipulation operations carried out by the force measurement assemblies of the systems of FIGS. 1-6, according to an embodiment of the invention.

FIG. 10 graphically illustrates the acquisition and processing of the load data carried out by the illustrative embodiments of the force measurement systems 100, 200, 300 of FIGS. 1-9. Initially, as shown in FIG. 10, a load L is applied to the force measurement assemblies 10, 10', 10" by a subject disposed thereon. The load is transmitted from the top plates 34 of the active force measurement assemblies 10, 10', 10" to their respective set of pylon-type force transducers 36 or force transducer beams. As described above, in one embodiment of the invention, each top plate 34 comprises four (4) pylon-type force transducers 36 disposed thereunder (e.g., see FIG. 7). Preferably, these pylon-type force transducers are disposed near respective corners of each top plate component 34. In a preferred embodiment of the invention, each of the pylon-type force transducers 36 includes a plurality of strain gages wired in one or more Wheatstone bridge configurations, wherein the electrical resistance of each strain gage is altered when the associated portion of the associated pylon-type force transducer undergoes deformation (i.e., a measured quantity) resulting from the load (i.e., forces and/or moments) acting on the top plate component 34. For each plurality of strain gages disposed on the pylon-type force transducers 36, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 36 disposed under each top plate component 34 output a total of four (4) analog output voltages (signals). In another embodiment, the four (4) pylon-type force transducers 36 disposed under each top plate component 34 output a combined total of three (3) analog output voltages (signals). In some embodiments, the three (3) or four (4) analog output voltages from each top plate component 34 are then transmitted to a preamplifier board (not shown) for preconditioning. The preamplifier board is used to increase the magnitudes of the transducer analog voltages, and preferably, to convert the analog voltage signals into digital voltage signals as well. After which, each force measurement assembly 10, 10', 10" transmits the force plate output signals $S_{FPO1}$-$S_{FPO4}$ to a main signal amplifier/converter 50. Depending on whether the preamplifier board also includes an analog-to-digital (A/D) converter, the force plate output signals $S_{FPO1}$-$S_{FPO4}$ could be either in the form of analog signals or digital signals. The main signal amplifier/converter 50 further magnifies the force plate output signals $S_{FPO1}$-$S_{FPO4}$, and if the signals $S_{FPO1}$-$S_{FPO4}$ are of the analog-type (for a case where the preamplifier board did not include an analog-to-digital (A/D) converter), it may also convert the analog signals to digital signals. Then, the signal amplifier/converter 50 transmits either the digital or analog signals $S_{ACO1}$-$S_{ACO4}$ of each force measurement assembly 10, 10', 10" to the data acquisition/data processing device 40 (computer or computing device 40) so that the forces and/or moments that are being applied to the top surfaces 22, 22', 22" of the force measurement assemblies 10, 10', 10" can be transformed into output load values or output load data OL that can be used to determine, for example, the vertical ground reaction force and the center of pressure (COP) of the subject. For example, as shown in FIG. 8, the center of pressure (COP) of the point of application of the force may be determined in accordance with the x and y coordinate axes 150, 152 (i.e., a set of center of pressure coordinates $x_p$, $y_p$ may be determined relative to the x and y coordinate axes 150, 152). In addition to the components 40a, 40b, 40c, the data acquisition/data processing device 40 may further comprise an analog-to-digital (A/D) converter if the signals $S_{ACO1}$-$S_{ACO4}$ of each force measurement assembly 10, 10', 10" are in the form of analog signals. In such a case, the analog-to-digital converter will convert the analog signals into digital signals for processing by the microprocessor 40a.

When the data acquisition/data processing device 40 receives the voltage signals $S_{ACO1}$-$S_{ACO4}$ from each force measurement assembly 10, 10', 10", it initially transforms the signals into output forces and/or moments by multiplying the voltage signals $S_{ACO1}$-$S_{ACO4}$ by a calibration matrix. After which, the vertical force $F_Z$ exerted on the top surface 22, 22', 22" of each active force measurement assembly 10, 10', 10" by the feet of the subject and the center of pressure for the subject (i.e., the x and y coordinates of the point of application of the force applied to the measurement surface by each foot) are determined by the data acquisition/data processing device 40.

While, in one exemplary embodiment, the data acquisition/data processing device 40 determines the vertical force $F_Z$ exerted on the top surface 22, 22', 22" of each active force measurement assembly 10, 10', 10" by the feet of the subject and the center of pressure for the subject, it is to be understood that the invention is not so limited. Rather, in other embodiments of the invention, the output forces of the data acquisition/data processing device 40 could include all three (3) orthogonal components of the resultant forces ($F_X$, $F_y$, $F_z$) acting on each active force measurement assembly 10, 10', 10". In yet other embodiments of the invention, the output forces and moments of the data acquisition/data processing device 40 can be in the form of other forces and moments as well (i.e., all six (6) orthogonal force and moment components, namely $F_x$, $F_y$, $F_z$, $M_x$, $M_y$, $M_z$).

It is readily apparent that the embodiments of the force measurement system 100, 200, 300 described above offer numerous advantages and benefits. First of all, the embodiments of the force measurement system 100, 200, 300 explained herein employ a compact arrangement of force plates that is capable of accurately assessing the gait of a subject when the subject walks or runs on the force measurement system. Secondly, the embodiments of the force measurement system 100, 200, 300 described above do not have the leg crossing problems associated with dual-belt instrumented treadmills because the force measurement assemblies 10, 10', 10" illustrated above span the full step width of the subject. Finally, the embodiments of the afore-described force measurement system 100, 200, 300 do not have the belt seam problems that are associated with instrumented treadmills having posteriorly and anteriorly located belts.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system for assessing the gait of a subject, comprising, in combination:
  a plurality of force measurement assemblies arranged in a loop configuration, the plurality of force measurement assemblies configured to be displaced around a continuous path of movement such that a particular one of the plurality of force measurement assemblies that is disposed underneath the subject varies over time, each of the plurality of force measurement assemblies including:
    a top surface for receiving at least one portion of the body of the subject; and
    at least one force transducer, the at least one force transducer configured to sense one or more measured quantities and output one or more signals that are representative of forces and/or moments being applied to the top surface of the force measurement assembly by the subject; and
  a plurality of linkage assemblies, each of the plurality of linkage assemblies being connected to adjacent force measurement assemblies of the plurality of force measurement assemblies and supporting the top surfaces of the connected adjacent force measurement assemblies so as to remain generally parallel as the plurality of force measurement assemblies are displaced around the continuous path of movement, wherein, when the plurality of force measurement assemblies are displaced around the continuous path of movement, each of the plurality of force measurement assemblies remains generally parallel to each other of the plurality of force measurement assemblies and wherein each of the plurality of force measurement assemblies is attached to at least one continuous coupling member or assembly, the at least one continuous coupling member or assembly being configured to rotate about at least two space-apart, generally horizontal rotational axes.

2. The force measurement system according to claim 1, wherein the at least one continuous coupling member or assembly is guided over at least two spaced-apart rotary elements, each of the at least two spaced-apart rotary elements configured to rotate about a respective one of the at least two spaced-apart, generally horizontal rotational axes.

3. The force measurement system according to claim 2, wherein each of the at least two spaced-apart rotary elements comprises one of: (i) a roller, (ii) a gear member, and (iii) a pulley.

4. The force measurement system according to claim 1, wherein, as the plurality of force measurement assemblies are displaced around the continuous path of movement, an elevation of the top surfaces of each of the plurality of force measurement assemblies changes relative to a support surface on which the force measurement system is disposed.

5. The force measurement system according to claim 1, wherein the plurality of force measurement assemblies are in the form of a plurality of force plates, and wherein a gap is provided between each of the plurality of force plates so as to prevent interaction between adjacent ones of the plurality of force plates.

6. The force measurement system according to claim 1, further comprising a data processing device operatively coupled to each of the force transducers of each of the force measurement assemblies, the data processing device configured to receive each of the one or more signals that are representative of the one or more measured quantities and to convert the one or more signals into load output data, the load output data comprising one or more forces and one or more moments.

7. A force measurement system for assessing the gait of a subject, comprising:
  a plurality of force measurement assemblies arranged in a loop configuration, the plurality of force measurement assemblies configured to be displaced around a continuous path of movement such that a particular one of the plurality of force measurement assemblies that is disposed underneath the subject varies over time, each of the plurality of force measurement assemblies including:
    a top surface for receiving at least one portion of the body of the subject; and
    at least one force transducer, the at least one force transducer configured to sense one or more measured quantities and output one or more signals that are representative of forces and/or moments being applied to the top surface of the force measurement assembly by the subject; and
  a data processing device operatively coupled to each of the force transducers of each of the force measurement assemblies, the data processing device configured to receive each of the one or more signals that are representative of the one or more measured quantities and to convert the one or more signals into load output data, the load output data comprising one or more forces and one or more moments; and
  a plurality of linkage assemblies, each of the plurality of linkage assemblies being connected to adjacent force measurement assemblies of the plurality of force measurement assemblies and supporting the top surfaces of the connected adjacent force measurement assemblies so as to remain generally parallel as the plurality of force measurement assemblies are displaced around the continuous path of movement, wherein, when the plurality of force measurement assemblies are displaced around the continuous path of movement, each of the plurality of force measurement assemblies remains generally parallel to each other of the plurality of force measurement assemblies and wherein each of the plurality of force measurement assemblies is attached to at least one continuous coupling member or assembly, the at least one continuous coupling member or assembly being configured to rotate about at least two spaced-apart, generally horizontal rotational axes.

8. The force measurement system according to claim 7, wherein the plurality of force measurement assemblies are in the form of a plurality of force plates, and wherein a gap is provided between each of the plurality of force plates so as to prevent interaction between adjacent ones of the plurality of force plates.

* * * * *